US00PP32967P2

(12) United States Plant Patent
Lee

(10) Patent No.: US PP32,967 P2
(45) Date of Patent: Apr. 13, 2021

(54) ***RHODODENDRON* PLANT NAMED 'ROBLEZD'**

(50) Latin Name: ***Rhododendron* hybrid**
Varietal Denomination: ROBLEZD

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 16/602,844

(22) Filed: Dec. 10, 2019

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 6/364
See application file for complete search history.

*Primary Examiner* — Anne Marie Grunberg
(74) *Attorney, Agent, or Firm* — Cassandra Bright

(57) ABSTRACT

A new and distinct cultivar of *Rhododendron* plant named 'ROBLEZD' is disclosed, characterized by light lavender, semi-double flowers. Plants are compact, reblooming and flower abundant. The new cultivar is a *Rhododendron*, suitable for ornamental garden purposes.

2 Drawing Sheets

Figure 1:
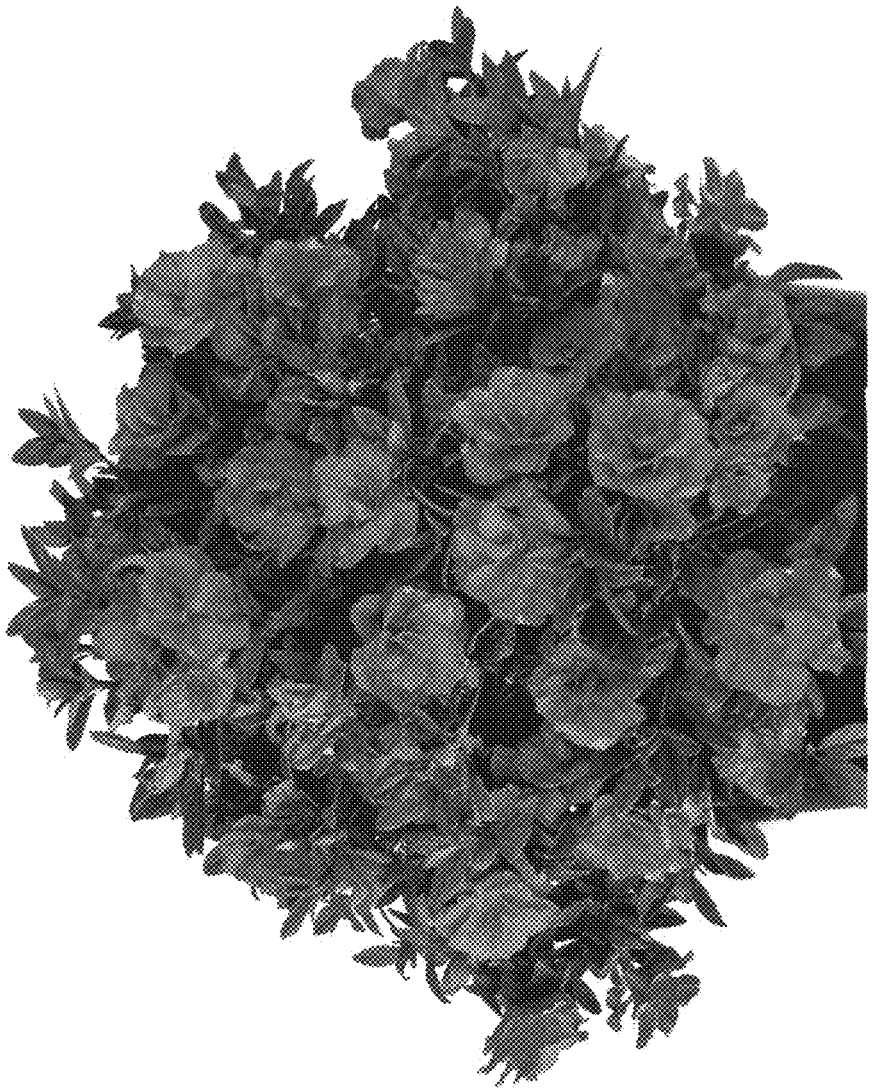

Latin name of the genus and species: *Rhododendron* hybrid.

Variety denomination: 'ROBLEZD'.

BACKGROUND OF THE INVENTION

The new cultivar is a product of field pollination. This new variety, hereinafter referred to as 'ROBLEZD', was discovered as a seedling, resulting from seed collected from *Rhododendron* 'Robleb', U.S. Plant Pat. No. 13,681. The pollen parent is unidentified as numerous unpatented *Rhododendron* varieties were in the field. The pollination resulting in the new variety occurred during Spring of 2008. The new variety was selected by the inventor during Autumn of 2011 at a nursery in Independence, La.

After identifying the new variety as a potentially interesting selection, the inventor first organized propagation of 'ROBLEZD' by semi-softwood cuttings during Autumn of 2011 at the same nursery in Independence, La. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEZD' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEZD' These characteristics in combination distinguish 'ROBLEZD' as a new and distinct *Rhododendron* cultivar:

1. Unique light lavender flower color.
2. Semi-double blooms.

3. Re-Blooming habit
4. Compact plants.
5. Abundant flowering.

COMPARISON TO PARENT VARIETY

'ROBLEZD' is similar in most horticultural characteristics to the seed parent, however, plants of the new cultivar 'ROBLEZD' however differ in the following:

1. The new variety has light lavender flowers, while the seed parent has red flowers.
2. The new variety has semi-double flowers, while the seed parent has single to semi-double flowers.
3. The new variety is more compact, while the seed parent is more upright.

COMMERCIAL COMPARISON

'ROBLEZD' can be compared to the commercial variety *Rhododendron* hybrid 'RLH1-14P14', U.S. Plant Pat. No. 24,751. Plants of the new cultivar 'ROBLEZD' are similar to plants of 'RLH1-14P14' in most horticultural characteristics, however, plants of the new cultivar 'ROBLEZD' differ in the following:

1. Flowers of 'Roblezd' have more petals, resulting in a semi-double bloom, compared to the single flower of this comparator.
2. Plants of the new variety are more compact then plants of this comparator.
3. Plants of the new variety produce more flowers than plants of this comparator.

'ROBLEZD' can be compared to the commercial variety *Rhododendron* hybrid 'Robles', U.S. Plant Pat. No. 22,762. Plants of the new cultivar 'ROBLEZD' are similar to plants of 'Robles' in most horticultural characteristics, however, plants of the new cultivar 'ROBLEZD' differ in the following:

1. Flowers of 'Roblezd' have more petals, resulting in a semi-double bloom, compared to the single flower of this comparator.
2. Plants of the new variety are more compact then plants of this comparator.
3. Plants of the new variety produce more flowers than plants of this comparator.

BRIEF DESCRIPTION OF THE PHOTOGRAPHS

The accompanying photograph in FIG. 1 illustrates in full color a typical plant of 'Roblezd' in a 2 gallon nursery container at approximately 3 years of age.

Figure 2:
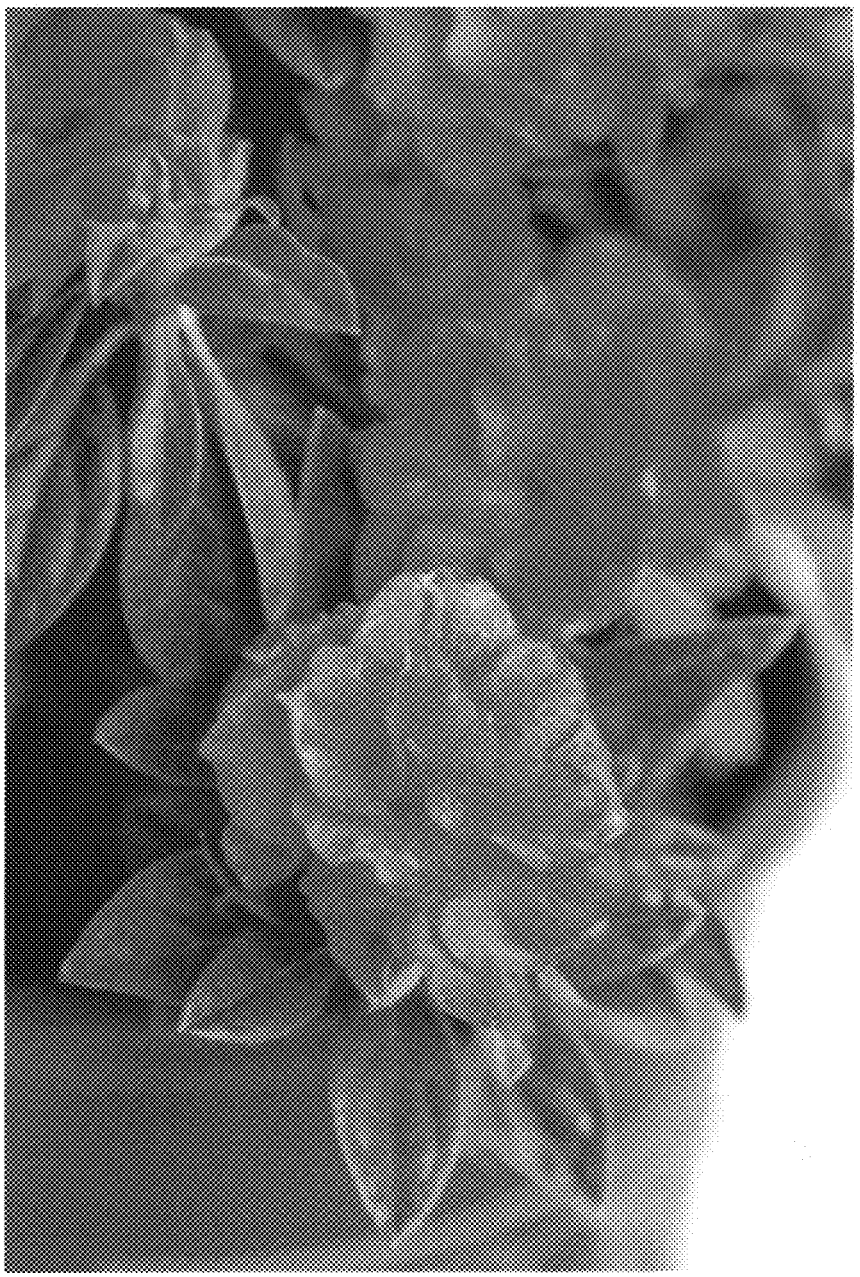

FIG. 2 illustrates a close up of a typical inflorescence of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ROBLEZD' plants grown outdoors in Loxley, Ala. Plants are approximately 2 years old, in a 3 gallon nursery container. Measurements and numerical values represent averages of typical plant types.

Botanical classification: *Rhododendron* hybrid 'ROBLEZD'.

PROPAGATION

Typically by semi-hardwood cuttings in Spring and Summer.

Root description: Fine, fibrous young roots, well branched. Colored near RHS Grey-Brown 199A.

PLANT

Growth habit: Compact , globular shrub.

Height: Approximately 35 cm to top of foliar and flowering plane.

Plant spread: Approximately 50 cm.

Branching characteristics: Well branched, approximately 4 to 6 primary branches from the center of the plant. Branches occur at approximately 45° to 75° angles. Each primary branch has 2 to 6 lateral branches.

Primary branches:

Length of primary branches: Average range 15 to 20 cm.

Diameter of primary branches: Approximately 7 mm.

Primary branch strength: Very strong, difficult to break.

Primary branch color: Young primary branches near RHS Yellow-Green 146A; oldest branches become woody, colored near Brown 200C streaked Grey-Brown 199C.

Primary branch texture: Immature growth hirsute. Older growth scaly, hirsute.

Lateral branches:

Number of lateral branches: Approximately 2 to 6 per primary branch.

Length of lateral branches: Average 5 to 10 cm.

Diameter of lateral branches: Average 4 mm.

Lateral branch strength: Very strong, flexible.

Lateral branch color: Immature branches near RHS Yellow-Green 146A flushed Greyed-Purple 183A, turning, Greyed-Orange 175C.

Lateral branch texture: Hirsute.

Internode length: Average range 1.0 to 3.0 cm.

Age of plant described: Approximately 2 years.

FOLIAGE

Leaf:

*Type*.—Simple.

*Arrangement*.—Alternate.

*Average length*.—Approximately 5.4 cm.

*Average width*.—Approximately 2.4 cm.

*Shape of blade*.—Obovate.

*Apex*.—Mucronate.

*Base*.—Broad attenuate.

*Attachment*.—Stalked.

*Margin*.—Entire.

*Texture of top surface*.—Pubescent. Hairs appressed.

*Texture of bottom surface*.—Pubescent. More hairs present along main vein and margin.

*Color*.—Young foliage upper side: Near RHS Yellow-Green 144A. Young foliage under side: Near RHS Yellow-Green 145A. Mature foliage upper side: Near RHS Green 139A. Mature foliage under side: Near RHS Green 138A.

*Venation*.—Type: Pinnate. Venation color upper side: Near RHS Yellow-Green N144A. Venation color under side: Near RHS Yellow-Green N144B.

Petiole:

*Length*.—About 7 mm.

*Diameter*.—About 2 mm.

*Color*.—Upper Surface: Near RHS Yellow-Green 148A. Lower Surface: Near RHS Yellow-Green 152C.

*Texture of top surface*.—Pubescent. Hairs appressed.

FLOWER

Bloom period: Plants begin flowering in the Spring, and continue to produce flowers throughout Summer and Fall.

Flower:

*Arrangement*.—Axillary clusters of perfect, double open funnel shaped individual flowers. Typically 3 to 7 flowers per cluster.

Inflorescence:

*Height*.—Average 9.0 cm.

*Diameter*.—Average 10.0 cm.

Peduncle:

*Length*.—Average 2.2 cm.

*Diameter*.—3 mm.

*Color*.—Near RHS Greyed-Orange 177A.

*Texture*.—Densely pubescent.

*Aspect*.—Straight. Angle of attachment, approximately 35° angle from stem.

Pedicel:

*Length*.—Average range 1.5 to 3.0 cm.

*Diameter*.—3 mm.

*Color*.—Near RHS Red 51A.

*Texture*.—Densely pubescent.

*Aspect*.—Straight. Angle of attachment, approximately 35° angle from stem.

Flowers:

*Length*.—Average 2.5 cm.

*Diameter*.—Average 4.2 cm.

*Facing direction*.—Outwardly and upwardly facing.
*Persistent or self-cleaning*.—Petals self-cleaning.
*Fragrance*.—Very faint, sweet scent.

Tube:
*Tube length*.—Approximately 9 mm.
*Tube width a widest point*.—Approximately 1.1 cm.
*Tube width and narrowest point*.—Approximately 4 mm.

Petals:
*Unfused petal segments*.—Length: Approximately 2.2 cm. Width: Approximately 1.8 cm.
*Apex*.—Blunt, rounded with shallow, irregular lobes. Occasionally retuse.
*Shape of petal*.—Unfused portion, obovate.
*Petal margin*.—Entire. Aspect very slightly undulating.
*Petal arrangement*.—Overlapping, bilateral symmetry dissecting bottom petal. Petals fused approximately ⅓ fused from base.
*Petal number*.—5.
*Petal texture*.—Smooth.
*Color*.—Upper surface at first opening: Near RHS Red-Purple N74C flushed Purple N78C. Linear speckles near Red-Purple 71A, about 2 to 3 mm long and 1 mm wide. Under surface at first opening: Near RHS Red-Purple N74C flushed N74B. Base near N74D. Inner surface at maturity: Near RHS Red-Purple 70B. Linear speckles near Red-Purple 71A, about 2 to 3 mm long and 1 mm wide. Outer surface at maturity: Near RHS Red-Purple 70B. Faint linear speckles near Red-Purple 71C, about 2 to 3 mm long and 1 mm wide. Upper surface at fading: Near RHS Red-Purple 72C. Linear speckles near Red-Purple 67A, about 2 to 3 mm long and 1 mm wide. Under surface at fading: Near RHS Red-Purple N74C. Linear speckles near Red-Purple 67A, about 2 to 3 mm long and 1 mm wide.

Bud:
*Shape*.—Elliptic.
*Length*.—1.8 cm.
*Diameter*.—1.0 cm.
*Color*.—Near RHS Red-Purple 71B.

Calyx/sepals:
*Quantity per flower*.—5 sepals.
*Shape*.—Narrow deltate.
*Length*.—5 mm.
*Width*.—2-3 3 mm.
*Apex*.—Acute.
*Base*.—Fused.
*Margin*.—Entire.
*Texture*.—Highly pubescent.
*Color*.—Inner Surface: Near RHS Yellow-Green 145A. Outer Surface: Near RHS Yellow-Green 145A.

REPRODUCTIVE ORGANS

Stamens:
*Number*.—2 full stamens.
*Length*.—1.6 cm.
*Width*.—1 mm.
*Color*.—Near RHS Red-Purple N74D.
*Anthers*.—Length: Approximately 1 mm. Color: Near RHS Red-Purple 71A. Pollen: Not observed.

Pistil:
*Number*.—1.
*Length*.—3.4 cm.
*Style*.—Length: Average 2.9 cm. Color: Near RHS Red-Purple 58C.
*Stigma*.—Globular, colored near RHS Red-Purple 59A.
*Ovary*.—Sericeous texture. Approximately 3 mm in diameter, 5 mm long. Colored near RHS Yellow-Green 145C.

OTHER CHARACTERISTICS

Disease and pest resistance: Not observed to be susceptible nor resistant to normal diseases and pests of *Rhododendron*.
Temperature tolerance: USDA Zone 6.
Fruit/seed production: Not observed to date.

What is claimed is:

1. A new and distinct cultivar of *Rhododendron* plant named 'ROBLEZD' as herein illustrated and described.

* * * * *